United States Patent [19]

Gupta

[11] 4,244,949

[45] Jan. 13, 1981

[54] MANUFACTURE OF LONG TERM CONTRACEPTIVE IMPLANT

[75] Inventor: Gopi N. Gupta, Blauvelt, N.Y.

[73] Assignee: The Population Council, Inc., New York, N.Y.

[21] Appl. No.: 894,088

[22] Filed: Apr. 6, 1978

[51] Int. Cl.² .............................................. A61K 31/56
[52] U.S. Cl. ................................................... 424/243
[58] Field of Search ........................................ 424/243

[56] References Cited

PUBLICATIONS

Shimkin and White, Absorption Rate of Hormone--Cholesterol Pellets, Endrocrinology, 29:1020, 1941.
P. M. F. Bishop, et al, Absorption of Hormone Implants in Man, Lancet, Aug. 11, 1951, pp. 229-232.
Lipschutz, et al., Recovery of Fertility After Protracted Steroid-Induced Sterility in Mice, Nature, vol. 190, pp. 174-175 (1961).

*Primary Examiner*—Henry R. Jiles
*Assistant Examiner*—Robert C. Whittenbaugh
*Attorney, Agent, or Firm*—Brumbaugh, Graves, Donohue & Raymond

[57] ABSTRACT

This invention relates to a bioabsorbable fused implant for subcutaneous administration in mammals of a constant and effective amount of a steroid over a prolonged period comprising a solid dispersion of an effective amount of a steriod uniformly dispersed in a matrix of a lipoid carrier the weight of steroid to lipoid carrier being within the approximate range of 99:1 to 80:20, respectively, and to the method of manufacturing the fused implants.

12 Claims, 4 Drawing Figures

In vivo, release of $^3$H-d-NG radioactivity from a fused microimplant (4.45mm long; 2.38mm O.D and 41.8mm$^2$ surface-area, 21.70mg mass; 80% $^3$H-d-NG + 20% chol., w/w) into urine o——o and feces x---x of rat

FIG. 4

In vivo, release of $^3$H-NETA radioactivity from a bioabsorbable fused microimplant (size—2.4 × 5.8mm$^2$ surface-area and 36.5mg mass, 80% $^3$H-NETA + 20% chol., w/w) into urine o——o, x---x in monkey

MANUFACTURE OF LONG TERM CONTRACEPTIVE IMPLANT

BACKGROUND OF THE INVENTION

The present invention relates to bioabsorbable fused implants which are effective in administering hormones subcutaneously in mammals over a protracted time period, and to the method of manufacturing the fused implants.

Steroids are currently used for treating a variety of conditions in mammals, including cancer, endocrine and gynecological problems and the control of fertility.

A variety of methods and apparatus have been known as aids in controlling fertility in mammals, including humans. Some approaches of current interest are condoms, IUCD's, diaphrams, spermidical creams, jellies and foams, and tablets and pills containing various steroids to be administered orallyl. Many of these approaches to fertility control are not completely effective and some cause undesirable side effects as a result of administering sex hormones such as estrogen and progesterone, normally associated with pregnancy, to non-pregnant females. These side effects range from migraine headaches, vomiting, fatigue, nausea, and hypertension to a higher risk of heart attacks.

The administration of steroid sex hormones such as 19-norprogesterone derivatives is known to prevent luteinization, that is, the production of the corpus luteum, as well as preventing ovulation, that is, the release of an egg from the ovary. The anti-luteinizing and anti-ovulation effects of these hormones have been used for several years to induce reversible protracted sterility in mammals, including humans. Pincus, G., Chang, M. C. et al. *Endocrinol.* 59, 694 (1956) Rock, J., Garcia, C. R. et al. *Amer. J. Obst. and Gynecol.* 79, 758 (1960).

One of the experimental methods of administering steroid sex hormones has been through subcutaneous implants. See, for example, U.S. Pat. No. 3,800,038 to Rudel; Kincl, *Acta Endocrinologica* 64 (1970) 253–264 and Kochakian, *American J. Physiol.*, 145 549 (1945). The implantation of pellets under the skin is a well-established method of administering steroids and other compositions. In 1936, M. J. Shear, *American Journal of Cancer*, 26:322–332 (1936), reported the use of fused implants of cholesterol and a carcinogen to induce tumors in animals. P. M. Bishop, in *Lancet*, Aug. 11, 1951, pp. 229–232, in an article entitled "Absorption of Hormone Implants in Man" summarizes the use of implants and reports that in 1938 he recorded the effects of implanting a 14 mg. pellet of oestrone in an ovariectomised woman; in 1939, Salmon et al. treated menopausal women with oestrodiol-benzoate implants; Thorn and Firor in 1940 treated Addison's disease by implanting pellets of deoxycortone and found that their effect lasted 9 to 12 months; in 1943, Greenblatt studied the effect of androgen implants in women with functional menstrual disorders; in 1947, Zondek suggested the introduction of pellets deep in the vaginal mucosa to avoid undesirable general systemic effects from hormone treatment; and, in 1949, Vargas treated diabetics by the implantation of pellets of protamine-zinc insulin and cholesterol.

The implants used in these early experiments were made according to a method developed by, among others, Shear, supra; Organon Laboratories Ltd., England, and M. B. Shimkin and J. White, *Endocrinology*, 29:1020–25 (1941). According to this method, the proximal end of a Pyrex glass tube of a desired length and bore is fitted with a rubber cap and a tightly fitting steel wire is inserted into the tube through the rubber cap to act as a plunger. In order to prevent adhering of the implants to the walls, the glass is lightly oiled with liquid petrolatum. The desired quantity of the active chemical and other ingredients are mixed and melted in an oil bath. The resulting solution is drawn up into the lubricated glass tube by means of the wire plunger. As soon as the material solidifies in the tube, it is extruded by the plunger. The solid rod thus formed is divided into implants of desired size by means of a razor blade. The implants are then washed in ether and again in alcohol to remove the oil on the surface and to smooth the rough edges.

The implants are introduced into the subcutaneous tissue of the subject by means of a trocar fitted with a plunger. The implants fit into the trocar, and no preparatory skin incision is necessary.

The glass tubing method of making fused implants has several major disadvantages. The fused implants tend to adhere to the glass wall and the glass must be lubricated to allow for removal of the implants. The use of lubrication is a serious drawback in preparing implants for human use. Implants for use in humans must be highly purified, and the use of oils and petrolatum on the glass tubing wall introduces an unwanted and troublesome impurity which must be scrupulously removed before the implant is suitable for human use.

The glass tubing method of the prior art has additional problems when used specifically for producing steroid implants such as are used for fertility control. According to this method, the steroid mixture is melted in a system that is open to the atmosphere. Since in most steroid mixtures melting occurs at a temperature above 100° C., there is danger of thermal decomposition of the hormone. The presence of oxygen from the atmosphere quickly activates undesirable oxidation changes in the steroid. In addition, if the mixture is heated above 500° C., the Pyrex glass begins to soften and may impart further impurities to the molten steroid mixture.

The problem of thermal decomposition of the components of an implant must also be considered during sterilization. Sterilization is often accomplished by heating the object to 100° C. for 60 minutes. The glass tube method of manufacturing implants is carried out open to the atmosphere and heating the components of the implant in contact with the oxygen in the atmosphere causes further decomposition products which seriously impair the purity of the implant.

A further disadvantage of the glass-tubing method is that it generally produces a cylindrical implant. Studies have shown that an implant of ellipsoidal shape in cross section is preferred for many reasons. Since glass is rigid and non-pliable, it is difficult to form glass tubing in an elliptical shape. The inability to easily produce an ellipsoidal implant is a serious drawback of the glass tubing system.

In the past, the use of the fused implants as a means of administering medication, especially sex hormones, has met with the problem of controlling the release of the drug to obtain constant long-term release of the therapeutic agent. In some pellet compositions, the dissolution rate was too slow and not enough of the therapeutic compound was released to the patient's system or, on the contrary, the dissolution rate was too rapid, which resulted in overdosing and insufficient length of drug release. It has been reported by M. B. Shimkin and J. White, *Endocrinology*, supra, and others that by combining cholesterol with the active ingredients in the pellet a long-acting implant can be produced. It was observed by Kochakian supra that compressed cholesterol-hormone implants were absorbed more slowly and uniformly than pure pellets, and in 1961 A. Lipschutz and R. Iglesias, *Nature*, 190 p. 174 (1961), found that implants containing 20% 19-norprogesterone and 80% cholesterol induced protracted sterility in mice.

Several other researchers, including Kincl supra and Rudel in U.S. Pat. No. 3,800,038, have prepared fused hormone-cholesterol implants for use in preventing conception but they have had serious disadvantages. Kincl reported that the desired rate of release of an active ingredient in an implant could be obtained by manipulating the concentration of the compound, the dimension of the implant and the nature of the carrier phase but he reports that he was unable to obtain reproducable results and Kincl suggested that the problem might be due to the manner in which the mixtures were made. Kincl employed the glass tubing method of forming implants.

Rudel's process also used the glass tube method of making implants, but in addition, Rudel's fused pellets are formed from a eutectic mixture at low temperatures which further adds to the problems of manufacturing the pellets. The eutectic point is that point in melting two different crystal substances at which the crystal substances have the lowest possible melting point which is lower than the melting point of either of the pure compounds. The mixture which crystalizes at that point is called the eutectic mixture or the eutectic. The eutectic of a two component system such as Rudel used has a fine grain structure and is a mixture of two solid phases.

R. S. Smart, in a paper entitled "Liquid Crystalline Behaviour in Mixtures of Cholesterol with Steroid Hormone" *Nature*, 215 (1967) pp. 957-958, reports on the composition and characteristics of steroid hormone mixtures similar to those used by Rudel. Smart found that steroids in cholesterol mixtures caused anisotropic melts which gave rise to eutectics which in most cases had a composition of 1:1 steroid to hormone that is 50% steroid and 50% hormone.

Other than the data reported by Smart, the phase diagrams needed to establish the eutectic point are not available for mixtures of cholesterol and steroids. Since the transition phases and phase diagrams of the common synthetic protestins have not been reported, it is difficult to define and select compositions which will give a eutectic melt.

A further disadvantage of the fused implants reported by Kincl and Rudel is in their composition. Kincl's implants contained from 98-70% cholesterol and 2-30% progestational hormone and Rudel's implants contain from 40-75% cholesterol and from 60-25% hormone. Since both the Rudel and Kincl implants contain a high percentage of cholesterol and a relatively small amount of the steroid, the implants would have to be impractically large in order to supply an effective daily dose of the hormone. For example, 80-100 micrograms norethindrone per day are necessary to control fertility in human females. In order to provide this daily dose over a prolonged period of time, for example, 6 months, an implant composed of the Rudel and Kincl type cholesterol-steroid mixture would be too large for practical purposes.

It has now been found that a fused ellipsoidal shaped pharmaceutical implant comprising a solid dispersion of an effective amount of a steroid uniformly dispersed in a matrix of a suitable lipoid carrier such that the ratio of the steroid to the carrier is 99:1 to 80:20, respectively, provides an effective long-term implant for subcutaneous administration in mammals.

The present invention is directed to a novel fused implant which eliminates the problems and disadvantages of earlier fused steroid-lipid implants and to a method of implant manufacture.

Specifically, the fused implants of the present invention are a bioabsorbable fused pharmaceutical implant, preferably ellipsoidal in cross section, for subcutaneous administration in mammals designed to slowly release a constant and effective amount of a steroid over a prolonged period comprising a solid dispersion of an effective amount of a steroid uniformly dispersed in a matrix of a suitable lipoid carrier, such that the weight ratio of the steroid to the lipoid carrier being in the approximate range of 99:1 to 80:20, respectively.

The preferred size range of the implant is 4-8 mm in length and 2.4 mm in minimum diameter and 2.8 mm in maximum diameter. The preferred weight range of the implant is 24 mg-48 mg.

It has also been found that the implant of the present invention can be prepared by heating a mixture of pure steroid and a meltable lipoid carrier at a temperature above the melting point of the steroid and the lipoid carrier in an inert atmosphere.

Specifically, the implants of the present invention are manufactured by a process which comprises the steps of purifying the steroid, storing the purified steroid under an inert atmosphere preferably nitrogen, loading a mixture of the pure steroid and the pure lipoid carrier into a thin walled tube of suitable length and diameter made from a flexible inert plastic having a non-stick surface, preferably a fluorocarbon resin such as Teflon[1], compacting the ingredients in the tube, heating the tube at a temperature above the melting point of the steroid and the lipoid carrier to fuse the mixture, and allowing the tube to cool, each step being carried out in an inert atmosphere preferably nitrogen and under aseptic conditions.

[1]Teflon is a trademark for polytetrafluorethylene registered by Du Pont.

In a preferred embodiment of the invention, a single implant is made. Sufficient steroid and carrier to prepare one implant are loaded under an inert atmosphere into a piece of fluorocarbon resin tubing approximately 10 cm in length, 2.4 mm in minimum diameter and 2.8 mm in maximum diameter, compacted and then heated on an aluminum block, preheated to a temperature above the melting point of the steroid. The tubing is then allowed to cool. This procedure yields a single fused ellipsoidal implant which can be removed from the tubing and stored under inert aseptic conditions or stored directly in the tubing under inert aseptic conditions.

In an alternative embodiment, multiple implants of random size are prepared. 1-2 grams of a suitable steroid and carrier are loaded under an inert atmosphere into a U-shaped piece of ellipsoidal fluorocarbon resin tubing approximately 25-27" in length, evacuated and flushed with an inert gas such as nitrogen. The U-shaped tube is heated in an oil bath, preheated above the melting point of the steroid, for 2 minutes. On cooling, multiple pellets of various sizes are formed and can be removed under aseptic conditions, graded and cut to desired lengths or they can be stored directly in the tubing under inert aseptic conditions.

The fused implants of the present invention may contain a steroid selected from the group consistion of: 17α-hydroxyprogesterone caproate, medroxyprogesterone acetate, megestrol acetate, melengestrol acetate, anagestone acetate, medrogestone, droxone, quingestrone, proligestone, chlormadinone acetate, chlorsuperlutin, Δ-chlormadinone acetate, cyproterone acetate, chlomethcrone, haloprogesterone, fluorgestone, clogestone, gestaclone, gestonorone caproate, methynodiol acetate, oxogestone, amidinone, R-5020, dimethisterone, ethisterone, allylestrenol, ethynerone, ethynodiol diacetate, lynestrenol, norethisterone, norethisterone acetate, norethisterone oenanthate, norethynodrel, norgestrienone, norvinodrel, quingestanol acetate, retroprogesterone, dydrogesterone, trengestone, 4-azidonorethisterone, cingestol, R-2323, d-norgestrel, norethindrone, norethindrone acetate, ethynydiol diacetate, norethandrolone, ethinyloestradiol, mestranol, quinestrol, estrofurate, esrazinol hydrobromide, estramustine phosphate, BDH 10131, sodium oestrone sulphate, piperazine oestrone sulphate, oestrone, equilenin, equilin, oestriol, quinestradol, epimestrol, oestriol succinate, stilboestrol, fosfestrol, dienoestrol, hexoestrol, benzoestrol, promestrol dipropionate, chlorotrianisene, methallenestril, clomiphene citrate, cyclofenil, MER-25, ICI-46,474, P 1496, testosterone, analogues of testosterone, cortisone and analogues of cortisone. The chemical structures for some of these compounds can be found in *Sex Hormone Pharmacology*, J. Brotherton, 1976, pp. 5-8.

The fused implant of the present invention also contains a lipoid carrier selected from the group consisting of: Cholesterol and its organic carboxylic esters containing from 1-20 carbon atoms.

The preferred implant of this invention contains a synthetic contraceptive progestin selected from the group consisting of d-norgestrel (NG), norethindrone (NET) and norethindrone acetate (NETA), with cholesterol as the lipoid carrier.

The steroids and lipoid carriers of the present invention are bioabsorbable, that is, can be totally absorbed by the host's body. Because of this feature, the implants of the present invention need not be removed from the host once it is implanted, since it is eventually totally absorbed by the host's body, and thus eliminates the need for surgical removal of the implant.

The method of manufacture using fluorocarbon resin tubing has several advantages, one of which is that it is flexible and implants with ellipsoidal cross sectioned design can be readily manufactured. Thin walled fluorocarbon tubing is preferred and it can be made ellipsoidal by pressing against the tubing wall with a stick or other suitable instrument.

Although the size of the needle required for insertion of the implant is governed by the size of the largest diameter of the ellipsoidal implant, the overall stretching of the skin is reduced by using an ellipsoidal shaped implant. The slightly flat elliptical shape of the implant reduces bulging when the implant is placed under the skin while retaining approximately the same surface area as a cylindrical implant. An implant in the form of an ellipsoidal cylinder of dimensions of, for example, 5 mm in length, lies flat under the skin in the subcutaneous fatty tissue layer creating a better physical-morphological condition for absorption. The rounded edges of an ellipsoidal implant prevents it from bulging under the skin and thereby creates less irritation and foreign body tissue reaction under the skin following implantation. On the other hand, the cylindrical pellet formed from the glass tube method lacks these benefits and as such, the glass tube method is a less desirable method of preparing fused implants for human implantation.

The ellipsoidal cross sectional design is the preferred form for the novel implant since it provides a more constant release of the active ingredient from the implant than an implant uniformly circular in cross section. The fact that a disc or slab shaped device will give more constant release than a cylinder shaped device is discussed in *Controlled Release Polymeric Formulations*, edited by D. R. Paul and F. W. Harris, ACS Symposium Series 33, American Chemical Society, Washington, D.C. 1976; Emmens, C. W., *Endocrinology* 28:633, 1941, pp. 633–642 and Shimkin, M. B. et al., Endocrinology, Vol. 35, 1944, pp. 283–295.

The primary feature governing the release from the implant is the surface area. The relationship is expressed by the Noyes-Whitney equations:

$$da/dt = KS \, (C_s - c),$$

where
- $a$ = the amount of drug dissolved in time t,
- $K$ = solution rate constant of the drug,
- $S$ = surface area of the solid pellet,
- $C_s$ = concentration of the drug in the diffusion layer surrounding the pellet
- $c$ = concentration of the drug in the dissolution medium.

A further advantage of the fused implants prepared by the method of the present invention is that, with proper precautions, they are sterile when made and can be directly inserted into the host without further treatment. When the implants are manufactured by a fusion method in fluorocarbon resin tubing at a temperature 5°–10° C. above the melting point of the highest individual component, the implants are sterile both on the surface and in the interior.

The fusion method of the present invention has many other advantages over the prior art glass tubing method. Unlike the prior art methods, the fusion in fluorocarbon resin tubing is carried out in an inert atmosphere, such as nitrogen, which enables the high temperature fusion reaction to proceed without oxidation of either the steroid or lipoid carrier. This feature allows for the production of a pure fused implant with no reaction impurities.

The fusion method of the present invention is also superior to the glass tubing method of fusion, in that once fused and solidified, the implants do not adhere to the side of the non-stick tubing and can be easily removed without the aid of oils or pretroleum jelly lubricants which are needed in the glass tubing method. This is a particularly important advantage when the implants are to be used for human implants since any traces of a foreign substance would cause serious problems when the implant is inserted subcutaneously. The implants can be removed by inserting a sterile plunger into the tubing or the tubing can be easily split using a razor blade or other knife-like objects for the easy removal of the implants under aseptic conditions.

A further advantage of using the fluorocarbon resin system is that these resins are inert under the conditions of the process and there is no interaction between the tubing walls and the organic compounds even at the high fusion temperatures. Since the fluorocarbon resin tubing is inert, flexible and unbreakable, the fused implants need not be removed from the tubing once they are formed but rather the tubing can be used as a convenient means of storing the fused implants under nitrogen.

In addition, when the system is used to manufacture a single implant, the fluorocarbon resin tubing can serve as part of a built-in trocar system for injecting the implant into the body. The fluorocarbon, polytetrafluoroethylene, such as Teflon, is particularly suited for this application since Teflon is used extensively for heart valve repair and replacements in humans, as well as in arterial and veinous replacements and it is known to be nontoxic and highly suited for insertion into the body.

The following will serve as non-limiting examples of the invention:

EXAMPLE 1

In accordance with one preferred embodiment of the invention, a single fused implant was produced as follows: The d-norgestrel, pharmaceutical grade was purchased from Wyeth Chemical Co. in micronized powder form. Five grams of the micronized powder were dissolved in 100 ml of a mixture of methanol and ethyl acetate, 8:2 by volume. The solution was filtered through analytical grade filter paper and crystallization of the d-norgestrel from the filtrate was initiated by slowly adding approximately 2 ml of distilled water. The mixture was allowed to slowly crystallize overnight in a refrigerator, then filtered through analytical grade filter paper. The crystals were dried under high vacuum at 60° C. to a constant weight for 2 or more hours. The dry d-norgestrel was stored under nitrogen at 25° C. for use in preparing the implant.

Cholesterol, certified grade having a guaranteed melting point of 148.0°–148.5° C. was purchased from Fisher Chemical Co. and used without any further purification.

A single ellipsoidal shaped fused pellet, 5 mm in length, was prepared as follows:

30 mg of the d-norgestrel crystals purified as described above and 7.5 mg of the Fisher certified cholesterol were crushed to a powder and thoroughly mixed. The mixture was flushed with nitrogen and transferred by means of a small funnel into a piece of specially prepared Teflon tubing. The tubing was ellipsoidal in cross section approximately 10 cm in length, 2.4 mm in minimum diameter, and 2.8 mm in maximum diameter, and was fitted at one end with a stainless steel probe having an ellipsoidal cross section conforming exactly to the inside dimensions of the Teflon tube. The tube was flushed with nitrogen and the open end of the tube was fitted with a second ellipsoidal shaped stainless steel probe and the two probes were moved toward each other to compress the powdered mixture. The portion of the tube containing the d-norgestrel and cholesterol mixture was heated on an aluminium block, preheated to 242° C. The melting point of d-norgestrel is 234°–235° C. The heating continued for 45 seconds, after which the probes were again pressed against the molten mass to consolidate the melt into one section of the tube. After heating for 45 seconds, during which the fashion takes place, the tube was cooled, and the probes were removed. The implant was removed under aseptic conditions by splitting the walls of the tubing using a sharp blade.

The implant was stored under aseptic conditions in a sealed glass ampule under nitrogen. In the alternative, the Teflon tubing was not split and the implant remained inside the tubing. The tubing plus implant then was stored in a glass ampule, preferably under nitrogen. The Teflon tubing with the implant inside was sterile because of the high fusion temperature used in preparing the implant. The Teflon tubing with the implant could then be used directly as a trocar for inserting the implant under a host's skin.

The fused d-norgestrel implant prepared according to this example is implanted and used as an effective contraceptive in mammals, such as rhesus monkeys. The implant releases 50–80 µg per day for one year or more.

EXAMPLE 2

Multiple fused implants of this invention were made according to an alternate procedure. Norethindrone was purified by dissolving 10 grams thereof in 180 ml of a mixture of methanol and ethyl acetate in 1:1 ratio by volume. The solution was filtered through analytical grade filter paper and crystallization of norethindrone was initiated by slowly adding about 2 ml of distilled water to the filtered solution. The norethindrone was allowed to crystallize in the refrigerator overnight. The crystals were filtered through analytical grade filter paper and then dried to constant weight at 60° C. under high vacuum for about 2 hours. The dry norethindrone was stored under nitrogen at 25° C. for use in preparing the implants.

Figure 1:
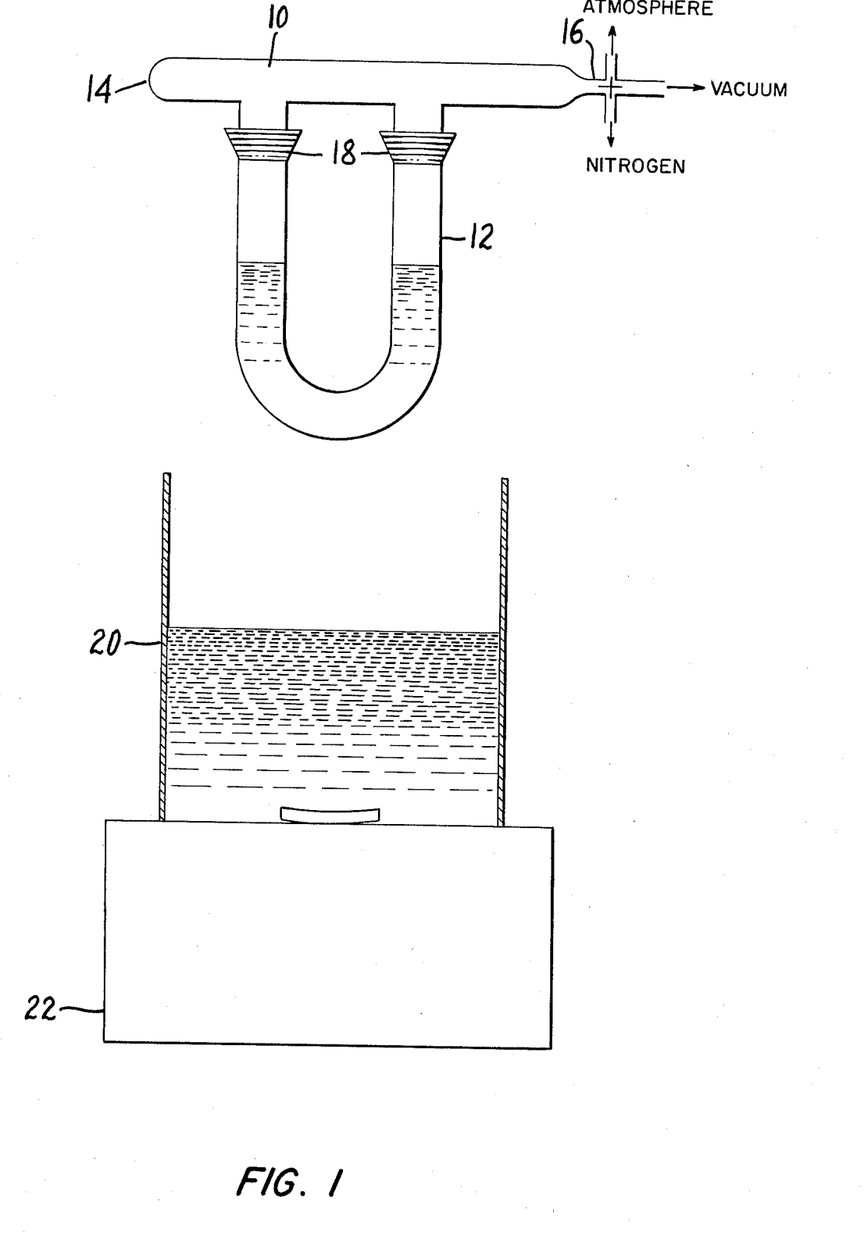
FIG. 1 shows the vacuum manifold used to prepare multiple pellets.

8.5 grams of norethindrone purified as above and 1.5 grams of Fisher certified cholesterol were crushed to a powder and thoroughly mixed. 2 grams of this mixture were transferred by means of a small funnel into both sides of a piece of No. 10 ellipsoidal Teflon tubing, approximately 27" in length, and the mixture is compacted in the tube by means of an electric vibrator. Referring to FIG. 1, the ends of the Teflon tubing 12 were attached to a double bore stainless steel vacuum manifold 10, which was sealed at one end 14 and attached to a vacuum source at the other end through a three-way stopcock 17. The Teflon tubing was attached to the manifold 10 and secured in place by aluminum couplings 18. The tubing and the manifold were mounted on a frame to lend stability and ease of handling. The U-shaped tubing 12 was evacuated through the three-way stopcock 16 and then flushed with nitrogen. This sequence was repeated at least 2–3 times and the tubing was then immersed for 2 minutes in an oil bath 20 which was preheated to 212° C. on a stirring hot plate 22. The melting point of the norethindrone was 203°–204° C. Fushion of the ingredients was complete after 2 minutes of heating. The tubing was taken out of the oil bath 20 and placed in an aseptic environment. After the tubing cooled, it was split open and fused implants in varying size fell out. The implants were graded into approximate sizes and cut into implants, approximately 5 mm in length and 2.4×2.8 mm in outer diameter. In the alternative, the tubing need not be split and the implants could be stored under aseptic conditions directly in the Teflon tubing.

The fused implant prepared according to this example is implanted and used as an effective contraceptive in mammals such as rhesus monkeys. The implant releases 40–70 μg per day for one year or more.

EXAMPLE 3

Multiple implants were prepared according to Example 2 using a 2 gram portion of a mixture containing 8.5 grams d-norgestrel purified as in Example 1 and 1.5 grams Fisher certified cholesterol. The fusion temperature was 242° C. for 2 minutes.

The implant is implanted and used as an effective contraceptive in mammals such as rhesus monkeys. The implant releases 50–80 μg per day for one year or more.

EXAMPLE 4

A single implant was prepared according to Example 1 using 30 mg of norethindrone purified as in Example 2 and 7.5 mg of Fisher certified cholesterol. The fusion temperature was 212° C. for 45 seconds.

The implant is implanted and used as an effective contraceptive in mammals such as rhesus monkeys. The implant releases 40–70 μg per day for one year or more.

EXAMPLE 5

Multiple implants were prepared according to Example 2 using a 2 gram portion of a mixture containing 8.5 grams norethindrone acetate purified (mp 161°–162° C.) as in Example 2 and 1.5 grams Fisher certified cholesterol. The fusion temperature was 169° C. for 2 minutes.

The implant is implanted and used as an effective contraceptive in mammals such as rhesus monkeys. The implant releases 90–120 μg per day for more than 6 months.

EXAMPLE 6

A single implant was prepared according to Example 1 using 30 mg of norethindrone acetate purified as in Example 1 and 7.5 mg of Fisher certified cholesterol. The fusion temperature was 169° C. for 45 seconds.

The implant is implanted and used as an effective contraceptive in mammals. The implant releases 90–120 μg per day for more than 6 months.

EXAMPLE 7

Multiple implants are prepared according to Example 2 using a 2 gram portion of a mixture containing 8.5 grams d-norgestrel purified as in Example 1, 0.85 grams mestranol crystallized from methanol and 1.5 grams Fisher certified cholesterol. The fusion temperature is 242° C. for 2 minutes.

EXAMPLE 8

A single implant is prepared according to Example 1 using 30 mg d-norgestrel purified as in Example 1, 3.0 mg mestranol crystallized from methanol and 5.3 mg Fisher certified cholesterol. The fusion temperature is 242° C. for 45 seconds.

EXAMPLE 9

Multiple implants are prepared according to Example 2 using a 2 gram portion of a mixture containing 8.5 grams norethindrone acetate purified as in Example 2, 0.85 grams mestranol crystallized from methanol and 1.5 grams Fisher certified cholesterol. The fusion temperature is 169° C. for 2 minutes.

EXAMPLE 10

A single implant is prepared according to Example 1 using 30.0 mg norethindrone acetate purified as in Example 2, 3.0 mg mestranol crystallized from methanol and 5.3 mg Fisher certified cholesterol. The fusion temperature is 169° C. for 45 seconds.

EXAMPLE 11

Multiple implants are prepared according to Example 2 using a 2 gram portion of a mixture containing 8.5 grams norethindrone purified as in Example 2, 0.85 grams mestranol crystallized from methanol and 1.5 grams Fisher certified cholesterol. The fusion temperature is 212° C. for 2 minutes.

EXAMPLE 12

A single implant is prepared according to Example 1 using 30 mg norethindrone purified as in Example 2, 3.0 mg mestranol crystallized from methanol and 5.3 mg Fisher certified cholesterol. The fusion temperature is 212° C. for 45 seconds.

EXAMPLE 13

Multiple implants are prepared according to Example 2 using a 2 gram portion of a mixture containing 8.5 grams d-norgestrel purified as in Example 1, 0.85 grams ethynylestradiol crystallized from methanol and water and 1.5 grams Fisher certified cholesterol. The fusion temperature is 242° C. for 2 minutes.

EXAMPLE 14

A single implant is prepared according to Example 1 using 30 mg d-norgestrel purified as in Example 1, 3.0 mg ethynylestradiol crystallized from methanol and water and 5.3 mg Fisher certified cholesterol. The fusion temperature is 243° C. for 45 seconds.

EXAMPLE 15

Multiple implants are prepared according to Example 2 using a 2 gram portion of a mixture containing 85 grams norethindrone purified as in Example 2, 0.85 grams ethynylestradiol crystallized from methanol and water and 1.5 grams Fisher certified cholesterol. The fusion temperature is 212° C. for 2 minutes.

EXAMPLE 16

A single implant is prepared according to Example 1 using 30 mg norethindrone purified as in Example 2, 3.0 mg ethynylestradiol crystallized from methanol and water and 5.3 mg Fisher certified cholesterol. The fusion temperature is 212° C. for 45 seconds.

EXAMPLE 17

Multiple implants are prepared according to Example 2 using a 2 grams portion of a mixture containing 8.5 grams norethindrone acetate purified as in Example 2, 0.85 grams ethynylestradiol crystallized from methanol and water and 1.5 grams Fisher certified cholesterol. The fusion temperature is 169° C. for 2 minutes.

EXAMPLE 18

A single implant is prepared according to Example 1 using 30 mg norethindrone acetate purified as in Example 2, 3.0 mg ethynylestradiol cystallized from methanol and water and 5.3 mg Fisher certified cholesterol. The fusion temperature is 169° C. for 45 seconds.

EXAMPLE 19

Multiple implants are prepared according to Example 2 using a 2 gram portion of a mixture containing 8.5 grams ethynodiol diacetate crystallized from methanol and water and 1.5 grams Fisher certified cholesterol. The fusion temperature is 134° C. for 2 minutes.

EXAMPLE 20

A single implant is prepared according to Example 1 using 30 mg ethynodiol diacetate crystallized from methanol and water and 5.3 mg Fisher certified cholesterol. The fusion temperature is 134° C. for 45 seconds.

EXAMPLE 21

Multiple implants are prepared according to Example 2 using a 2 gram portion of a mixture containing 8.5 grams hydrocortisone crystallized from absolute ethanol and 1.5 grams Fisher certified cholesterol. The fusion temperature is 228° C. for 2 minutes.

EXAMPLE 22

A single implant is prepared according to Example 1 using 30 mg hydrocortisone crystallized from absolute ethanol and 5.3 mg Fisher certified cholesterol. The fusion temperature is 228° C. for 45 seconds.

EXAMPLE 23

$H^3$ norethindrone was synthesized by the catalytic exchange method with carrier-free tritiated water ($^3H_2O$) by the following procedure: about 100 mg of norethindrone was dissolved in 0.5 to 1.0 ml of dimethylacetamide. To this was added 200 mg of 5% Rh/Al$_2$O$_3$ catalyst and 25 curies of carrier free tritiated water ($^3H_2O$). The reaction mixture was stirred overnight at 50° C. Labile ($^3H$) was removed in vacuo, using methanol as a solvent. The resulting $^3H$ norethindrone was filtered from the catalyst and taken to dryness to insure removal of labile ($^3H$). The product was taken up in 10 ml of methanol for additional purification. The total radioactivity of norethindrone at this state was about 500 millicuries. Further purification was accomplished by alumina column chromatography of the radioactive norethindrone. The column was prepared using a slurry of alumina prepared in benzene:methylalcohol (1:1) and the $^3H$ norethindrone was loaded on the column. A mixture of CHCl$_3$:MeOH (1:1) was used as an eluting solvent. This step was repeated three times. The final purification was accomplished by pooling the norethindrone fractions and evaporating the material to dryness under reduced pressure at 40°-50° C. The residue was dissolved in a minimum volume of MeOH, made slightly alkaline by 0.1 N NaOH, stirred and left for 15 minutes. Subsequently, the mixture was neutralized with 0.1 HCl.

The solvent was evaporated carefully under reduced pressure. To the dry residue was added 50 mg of unlabeled norethindrone. The material was dissolved once more in a minimum volume of CHCl$_3$:MeOH (1:1) mixture. The solution was transferred to a new alumina column (2 cm × 40 cm) for the final purification. The ($^3H$) norethindrone was eluted by CHCl$_3$:MeOH (1:1) mixture; 10 ml fractions were collected. The fractions of pure norethindrone peak were pooled, evaporated to dryness under N$_2$ and reduced pressure in a 60° C. waterbath. The dry residue material was placed at 60° C. under high vaccum for 2–3 hours. The pure and dry material was weighed and the radioactivity determined. The purity was checked by the isotopic-dilution and thin-layer chromatographic methods. The purity of $^3H$ norethindrone was found to be 98% to 100%. The specific activity was between 0.8 to 1 ci/mM. The amount of radioactivity isolated for purified $^3H$ norethindrone was 150 to 200 millicuries.

EXAMPLE 24

$^3H$-norgestrel was prepared according to the procedure in Example 23.

EXAMPLE 25

$^3H$-norethindrone acetate was prepared according to the procedure in Example 23.

EXAMPLE 26

(A) A single implant was prepared according to Example 1 using 32.90 mg of $^3H$ norethindrone prepared and purified according to Example 23 and 5.80 mg of Fisher certified cholesterol. The fusion temperature was 212° C. for 45 seconds and the implant had the characteristics as listed in Table I below.

(B) A single implant was prepared according to Example 1 using 30.32 mg of $^3H$ norethindrone prepared and purified according to Example 23 and 5.35 mg of Fisher certified cholesterol. The fusion temperature was 212° C. for 45 seconds and the implant had the characteristic as listed in Table I below.

(C) A single implant was prepared according to Example 1 using 32.16 mg of $^3H$ norethindrone prepared and purified according to Example 23 and 5.68 mg of Fisher certified cholesterol. The fusion temperature was 212° C. for 45 seconds and the implant had the characteristics as listed in Table I below.

(D) A single implant was prepared according to Example 1 using 32.86 mg of $^3H$ norethindrone prepared and purified according to Example 23 and 5.80 mg of Fisher certified cholesterol. The fusion temperature was 212° C. for 45 seconds and the implant had the characteristics as listed in Table I below.

Figure 2:
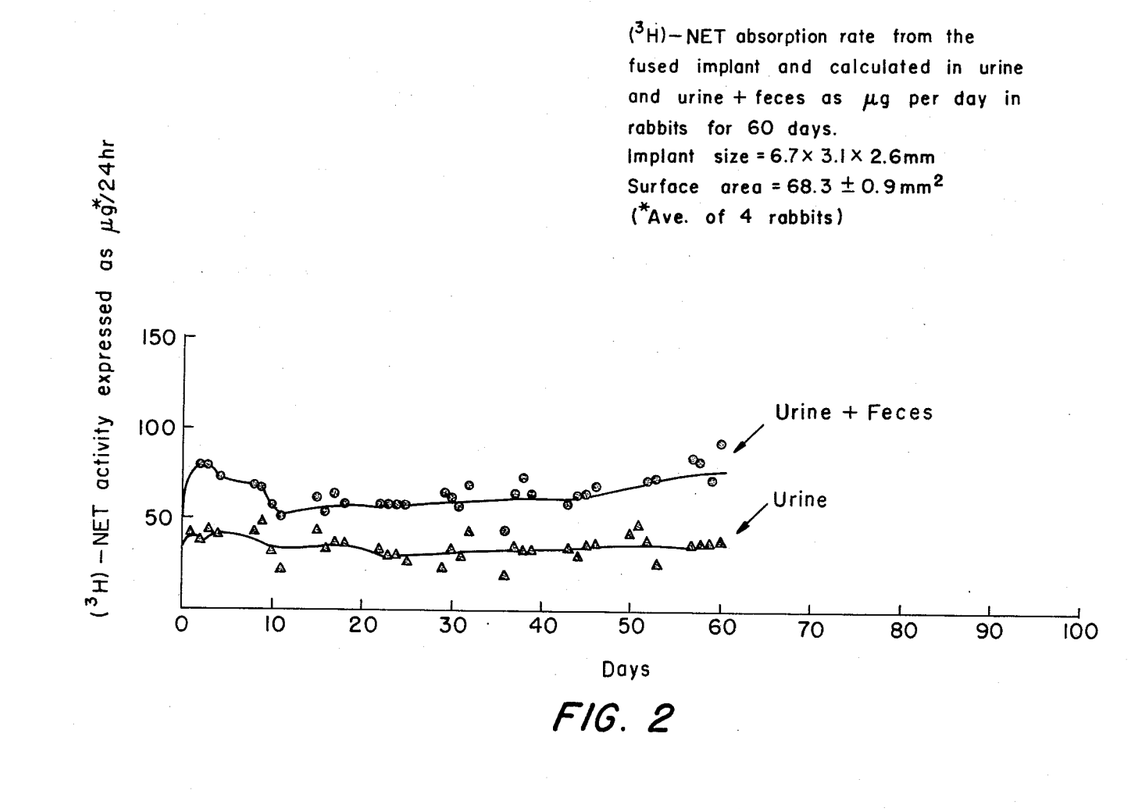
FIG. 2 shows the average absorption rate of $^3$H-NET from four in vivo implants as measured by the level of labeled material excreted in rabbit urine and urine plus feces.

Each implant from Example 26 as described in Table I was implanted in a New Zealand white rabbit and the absorption rate from the implant as measured by the level of labeled material excreted in urine and urine plus feces was calculated daily for 60 days and the daily average for the four rabbits was plotted as ($^3H$)NET activity expressed as μg/24 hours as as shown in FIG. 2. The graph shows that a constant release rate of 78 μg/day was observed for the 60-day period. It is believed that the release rate of 78 μg/day would remain substantially constant for up to one year. Similar results have been observed in rats and rhesus monkeys for $^3H$ NET.

TABLE I

Characteristics of 85% ³H-NET+Chol. ellipsoidal fused implants used in in vivo studies in Rabbits

| Example No. | Animal Group | Total Wt. (mg) | Length (mm) | Widths (mm) | Surface area (mm²) | Total Radio-activity (mci) |
|---|---|---|---|---|---|---|
| 26A | (Rabbit # 1-4) | 38.71 | 7.0 | 3.1 × 2.6 | 70.59 | 0.77 |
| 26B |  | 35.67 | 6.5 | " | 66.37 | 0.71 |
| 26C |  | 37.84 | 6.8 | " | 68.90 | 0.75 |
| 26D |  | 38.66 | 6.6 | " | 67.21 | 0.77 |
| | mean = | 37.7 ± 0.7 | 6.7 ± 0.1 | | 68.27 ± 0.9 | 0.75 ± 0.01 |

EXAMPLE 27

A single implant was prepared according to Example 1 using 17.36 mg ³H d-norgestrel purified and prepared as in Example 24 and 4.34 mg Fisher certified cholesterol. The fusion temperature was 242° C. for 45 seconds.

The implant was 4.45 mm long; 2.38 mm O.D. and 41.8 mm² surface-area and weighed 21.70 mg.

Figure 3:
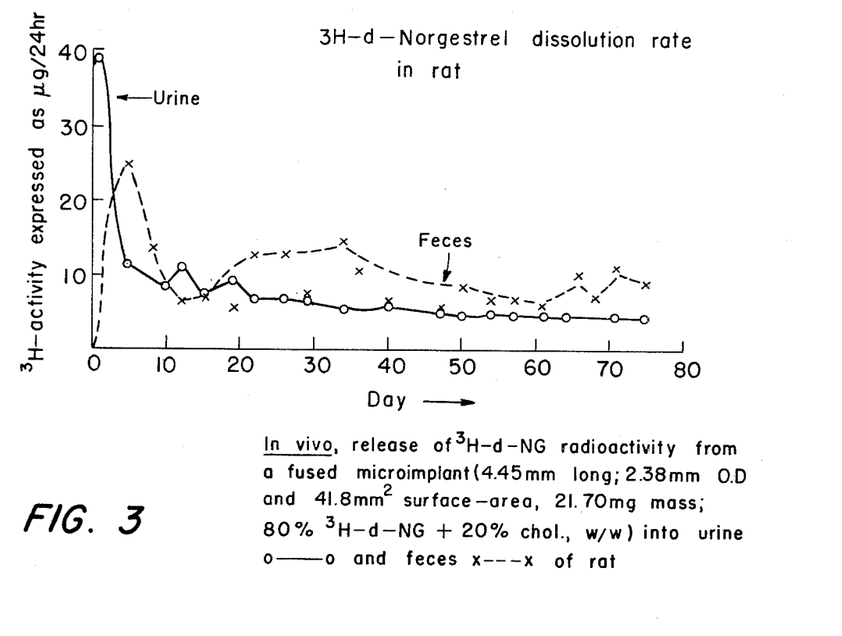
FIG. 3 shows the release of $^3$H-d-NG from an in vivo implant as measured by the level of labeled material excreted into rat unine and feces.

The implant was inserted with an 11-gauge trocar under the abdominal skin of an ether-anesthesized adult female rate of the Holtzman Colony. The release of (³H)-d-norgestrel from the implant as measured by the level of labeled material excreted into the feces and urine was measured. These results are given in FIG. 3 and show that after an initial release burst, a fairly constant total release of about 15 μg/day was observed for 75 days. Similar results have been observed in monkeys.

It is believed that the release rate of 15 μg/day would remain constant for up to 2 ½ years in the rat. The release rate for the implant prepared in this example is lower than in other examples because the dimensions of the implant are different from that used in the other examples. In addition, the release rate in the rat is usually lower than in the monkey and the rabbit, and accounts for the lower observed daily release rate.

EXAMPLE 28

A single implant was prepared according to Example 1 using 29.2 mg ³H norethindrone acetate purified and prepared according to Example 25 and 7.3 mg Fisher certified cholesterol. The fusion temperature was 169° C. for 45 seconds. The implant was 2.4×5.8 mm² surface-area and weighed 36.5 mg.

Figure 4:
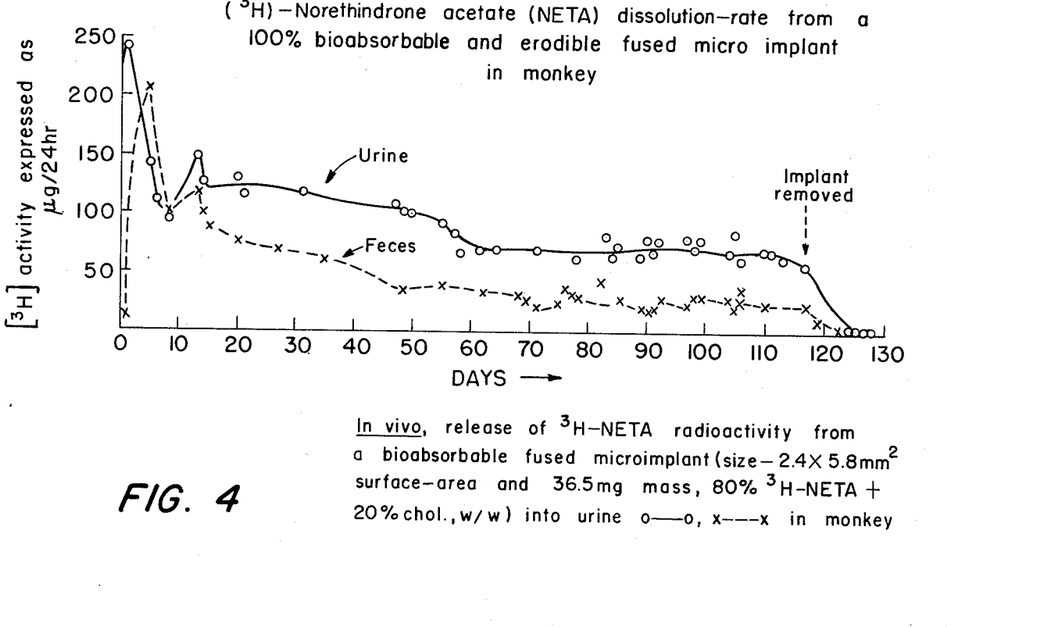
FIG. 4 shows the release of $^3$H-NETA from an in vivo implant as measured by the level of labeled material excreted into monkey urine and feces.

The implant was inserted in an adult female rhesus monkey selected from the Population Council, Rockefeller University Colony stock. The implant was placed subcutaneously in the ventral surface below the rib cage using an 11-guage trocar. The release of ³-H-NETA from the implant as measured by the level of radioactive material in the urine and feces was measured and plotted. The results are shown in FIG. 4. After an initial release burst, a fairly constant total release of about 100 μg per day was observed for a 110-day period. It is believed that the total release rate of 100 μg/day would remain substantially constant for up to 8 months.

I claim:

1. The process of preparing a fused implant for fertility control which comprises the steps of:
   (a) purifying an anti-ovulation sex hormone;
   (b) storing the purified anti-ovulation sex hormone
   (c) loading a finely divided mixture of pure anti-ovulation sex hormone and a pure lipoid carrier into a tube of a suitable diametermade from a flexible inert plastic having a non-stick surface;
   (d) compacting the ingredients in the tube;
   (e) heating the tube and the contents at a temperature above the melting point of the anti-ovulation sex hormone and the lipoid carrier to fuse the mixture; and
   (f) allowing the tube to cool, the steps (b)-(f) being conducted in an inert atmosphere and under aseptic conditions.

2. The process for preparing a fused implant as described in claim 1 wherein the cooled tube and contents are sealed in a glass ampule under inert atmosphere for storage.

3. The process as described in claim 1 wherein the tubing has an ellipsoidal cross section and is made from a polytetrafluoroethylene type resin.

4. The process as described in claim 1 wherein the tube and the contents are heated at a temperature 5°-10° C. above the melting point of the anti-ovulation sex hormone.

5. The process as described in claim 4 wherein the tube and contents are heated on a metal block for 45-60 seconds.

6. The process as described in claim 4 wherein the tube and contents are heated in an oil bath for 1.5-2 minutes.

7. The process of preparing a fused implant for fertility control which comprises the steps of:
   (a) purifying an anti-ovulation sex hormone;
   (b) storing the purified anti-ovulation sex hormone under nitrogen;
   (c) loading a mixture of finely divided pure anti-ovulation sex hormone and a finely divided pure lipoid carrier into a piece of tubing of suitable diameter made from a flexible inert plastic having a non-stick surface, fitted with a solid probe at one end;
   (d) placing a second solid probe in the open end of the tube and moving the two probes toward the solid;
   (e) heating the piece of tubing at a temperature above the melting point of the anti-ovulation sex hormone and the lipoid carrier to fuse the mixture;
   (f) moving the two probes to consolidate anti-ovulation sex hormone and carrier;
   (g) allowing the tube to cool;
   (h) removing the probes; and
   (i) storing the tube with the implant enclosed in a glass ampule, the steps (c)-(i) being conducted in a nitrogen atmosphere and under aseptic conditions.

8. The process as described in claim 7 wherein the tubing has an ellipsoidal cross section and is made from a polytetrafluoroethylene type resin.

9. The process as described in claim 7 wherein the tube is heated at a temperature 5–10° C. above the melting point of the anti-ovulation sex hormone.

10. The process as described in claim 1 wherein the tube and contents are heated on a metal block for 45–60 seconds.

11. The process of preparing a fused implant for fertility control which comprises the steps of:
   (a) purifying an anti-ovulation sex hormone selected from the group consisting of d-norgestrel, norethindrone and norethindrone acetate;
   (b) storing the purified anti-ovulation sex hormone under nitrogen;
   (c) loading a finely divided mixture of pure anti-ovulation sex hormone and a pure lipoid carrier into a tube of a suitable diameter made from a flexible inert plastic having a non-stick surface;
   (d) compacting the ingredients in the tube;
   (e) heating the tube and the contents at a temperature above the melting point of the anti-ovulation sex hormone and the lipoid carrier to fuse the mixture; and
   (f) allowing the tube to cool, the steps (b)–(f) being conducted in an inert atmosphere and under aseptic conditions.

12. The process of preparing a fused implant for fertility control which comprises the steps of:
   (a) purifying an anti-ovulation sex hormone selected from the group consisting of d-norgestrel, norethindrone and norethindrone acetate;
   (b) storing the purified anti-ovulation sex hormone under nitrogen;
   (c) loading a mixture of finely divided pure anti-ovulation sex hormone and a finely divided pure lipoid carrier into a piece of tubing of suitable diameter made from a flexible inert plastic having a non-stick surface, fitted with a solid probe at one end;
   (d) placing a second solid probe in the open end of the tube and moving the two probes toward the solid;
   (e) heating the piece of tubing at a temperature above the melting point of the anti-ovulation sex hormone and the lipoid carrier to fuse the mixture;
   (f) moving the two probes to consolidate the anti-ovulation sex hormone and carrier;
   (g) allowing the tube to cool;
   (h) removing the probes; and
   (i) storing the tube with the implant enclosed in a glass ampule, the steps (c)–(i) being conducted in a nitrogen atmosphere and under aseptic conditions.

* * * * *

UNITED STATES PATENT AND TRADEMARK OFFICE
CERTIFICATE OF CORRECTION

PATENT NO. : 4,244,949

DATED : January 13, 1981

INVENTOR(S) : Gopi N. Gupta

It is certified that error appears in the above—identified patent and that said Letters Patent is hereby corrected as shown below:

Col. 1, line 19, "orallyl" should read --orally--;

Col. 5, line 10, "Δ-chlormadinone" should read --Δ'-chlormadinone--;

Col. 5, line 11, "fluorgestone" should read --flurogestone--;

Col. 8, line 21, after "implant", second occurrence, insert -- inside --.

Col. 8, line 55, "17" should read --16--;

Col. 8, line 65, "Fushion" should read --Fusion--;

Col. 10, line 60, "grams" should read --gram--;

Col. 11, line 64, "0.1 HCl" should read --0.1 N HCl--;

Col. 12, line 9, "vaccum" should read --vacuum--;

Col. 12, line 41, "characteristic" should read --characteristics--;

Col. 13, line 53, "11-guage" should read --11-gauge--;

Col. 13, line 66, after "hormone" insert --under nitrogen--;

Col. 14, line 17, "diametermade" should read --diameter made--;

UNITED STATES PATENT AND TRADEMARK OFFICE
CERTIFICATE OF CORRECTION

PATENT NO. : 4,244,949
DATED : January 13, 1981
INVENTOR(S) : Gopi N. Gupta

It is certified that error appears in the above—identified patent and that said Letters Patent is hereby corrected as shown below:

Col. 14, lines 44-5, "fertilitty" should read --fertility--;

Col. 14, line 59, after "consolidate" insert --the--;

Col. 15, line 4, "claim 1" should read --claim 7--.

Signed and Sealed this

Twenty-sixth Day of May 1981

[SEAL]

Attest:

RENE D. TEGTMEYER

Attesting Officer     Acting Commissioner of Patents and Trademarks